US006407046B1

(12) United States Patent
Fowler et al.

(10) Patent No.: US 6,407,046 B1
(45) Date of Patent: *Jun. 18, 2002

(54) MUTANT EGIII CELLULASE, DNA ENCODING SUCH EGIII COMPOSITIONS AND METHODS FOR OBTAINING SAME

(75) Inventors: Timothy Fowler, Bainbridge Island, WA (US); Colin Mitchinson, Half Moon Bay, CA (US)

(73) Assignee: Genencor International, Inc., Palo Alto, CA (US)

(*) Notice: Subject to any disclaimer, the term of this patent is extended or adjusted under 35 U.S.C. 154(b) by 108 days.

This patent is subject to a terminal disclaimer.

(21) Appl. No.: 09/633,084

(22) Filed: Aug. 4, 2000

Related U.S. Application Data

(63) Continuation-in-part of application No. 09/146,770, filed on Sep. 3, 1998, now Pat. No. 6,187,732.

(51) Int. Cl.[7] .............................................. C11D 3/386
(52) U.S. Cl. ..................... 510/226; 510/320; 510/321; 510/392; 510/530; 8/116.1; 8/401; 435/209
(58) Field of Search ................ 510/226, 320, 510/321, 392, 530; 8/116.1, 401; 435/209; 426/635; 241/21

(56) References Cited

U.S. PATENT DOCUMENTS

| | | | |
|---|---|---|---|
| 4,738,682 A | 4/1988 | Boegh et al. | 510/320 |
| 4,832,864 A | 5/1989 | Olson | 510/530 |
| 5,068,009 A * | 11/1991 | Jokinen et al. | 162/9 |
| 5,246,853 A | 9/1993 | Clarkson et al. | 435/263 |
| 5,254,283 A | 10/1993 | Arnold et al. | 8/401 |
| 5,290,474 A | 3/1994 | Clarkson et al. | 8/401 |
| 5,475,101 A | 12/1995 | Ward et al. | 536/23.74 |
| 6,187,732 B1 * | 2/2001 | Fowler et al. | 510/226 |
| 6,268,328 B1 * | 7/2001 | Mitchinson et al. | 510/392 |

FOREIGN PATENT DOCUMENTS

| | | |
|---|---|---|
| EP | 220 016 | 8/1991 |
| EP | 271 004 | 4/1993 |
| FI | 87372 | 9/1992 |
| GB | 1358599 | 7/1981 |
| GB | 2075028 | 11/1981 |
| GB | 2094826 | 9/1982 |
| GB | 2095275 | 9/1982 |
| WO | WO 87 00863 A | 2/1987 |
| WO | WO 92/06209 | 4/1992 |
| WO | WO 94/14953 | 7/1994 |
| WO | WO 94/28117 | 12/1994 |
| WO | WO 95/16360 | 6/1995 |
| WO | WO 98/31821 | 7/1998 |

OTHER PUBLICATIONS

Chemical Abstracts, V. 84, N. 5, Feb. 2, 1976 (1976–02–02) Columbus, Ohio, Abstract No. 29189, Obata, Yasuo et al., "L–Ascorbic acid".

(List continued on next page.)

*Primary Examiner*—Gregory Delcotto
(74) *Attorney, Agent, or Firm*—Genencor International, Inc.

(57) ABSTRACT

The present invention relates to variant EGIII cellulases that have improved stability and/or performance. The variant cellulases have replacements at sensitive residues to improve stability and/or performance.

12 Claims, 5 Drawing Sheets

Amino Acid Sequence of Mature EGIII Protein

```
QTSCDQWATFTGNGYTVSNNLWGASAGSGFGCVTAVSLSGGASWHADWQWSGGQNNVKSY   60
QNSQIAIPQKRTVNSISSMPTTASWSYSGSNIRANVAYDLFTAANPNHVTYSGDYELMIW  120
LGKYGDIGPIGSSQGTVNVGGQSWTLYYGYNGAMQVYSFVAQTNTTNYSGDVKNFFNYLR  180
DNKGYNAAGQYVLSYQFGTEPFTGSGTLNVASWTASIN                        218
```

OTHER PUBLICATIONS

Haller C. et al., "Enzymatic synthesis of L–ascorbic acid 3. L–galactono–y–lactone Oxidase from yeasts," Dechema Biotechnology Conferences 4, VCH Verlagsgesellschaft 1990.

Hreggvidsson, et al., Appl. Environ. Microb. 62:3047 (1996).

Kiefer, et al., DNA and Cell Biol. 10:757 (1991).

Nagase, et al., DNA Research 2:37 (1995).

Nishikimi et al., "Occurrence in Yeast of L–Galactonolactone Oxidase Which is Similar to a Key Enzyme for Ascorbic Acid Biosynthesis in Animals, L–Gulonolactone Oxidase," Archives of Biochemistry and Biophysics, V. 191, No. 2, Dec., pp. 479–486, 1978.

Ooi, et al., Curr. Genet., 18:217 (1990).

Roberts, et al., AIDS Res. Hum. Retroviruses 12:593 (1996).

Roebroek, et al, EMBO J. 5 :2197 (1986).

Saarilahti, et al., Gene 90:9 (1990).

Sakamoto, et al., Curr. Genet. 27:435 (1995).

Seidah & Chretien, Methods In Enzymology, 244:175 (1994).

Smeekens & Steiner, J. Biol. Chem. 265:2997 (1990).

Tomkinson & Jonsson, Biochem. 30 :168 (1991).

Tomkinson & Zetterqvist, Biochem. J. 267:149 (1990).

Altschul, S. et al., "Basic Local Alignment Search Tool" (1990) J. Mol. Biol. Vol. 215, No. 3, pp. 403–410.

Ausubel, Frederick et al., "Short Protocols in Molecular Biology," Current Protocols in Molecular Biology, $2^{nd}$ ed., Greene Publishing Associates & John Wiley & Sons. New York, N.Y. 1992.

Bennett & Lasure (1991) "More Gene Manipulations in Fungi," Academic Press, San Diego, pp. 70–76.

Bergés, T. et al., "Isolation of uridine auxotrophs from Trichoderma reesei and efficient transformation with the cloned ura3 and ura5 genes" (1991) Curr. Genet. vol. 19, No. 5, pp. 359–365.

Berka, Randy M. et al., "The Development of Gene Expression Systems for Filamentous Fungi," Biotech. Adv. 7:127–154, 1989.

Burley, S. K. et al., "Aromatic–Aromatic Interaction: A Mechanism of Protein Structure Stabilization" (1985) Science 229: 23–29.

Eriksson, A. et al., "Response of a Protein Structure to Cavity–Creating Mutations and Its Relation to the Hydrophobic Effect" (1992) Science vol. 255, pp. 178–183.

Gloss, L. et al., "Urea and ThermalEquilibrium Denaturation Studies on the Dimerization Domain of Escherichia coli Trp Repressor" (1997) Biochem. Vol. 36, No. 19, pp. 5612–5623.

Karlin, S. et al., "Applications and statistics for multiple high–scoring segments in molecular sequences" (1993) Proc. Natl. Acad. Sci. USA vol. 90, No. 12, pp. 5873–5788.

Kellis, J. et al., "Contribution of hydrophobic interactions to protein stability" (1988) Nature vol. 333, pp. 784–786.

Knowles, J. et al., "Cellulase families and their genes" (1987) TIBTECH 5, pp. 255–261.

Luo, J. et al., "Detection of a Stable Intermediate in the Thermal Unfolding of a Cysteine–Free Form of Dihydrofolate Reductase from Escherichia coli" (1995) Biochem. Vol. 34, No. 33, pp. 10669–10675.

Matthews, B. et al., "Structural and Genetic Analysis of Protein Stability" (1993) Annu. Rev. Biochem. 62:139–160.

Needleman, S. et al., "A General Method Applicable to the Search for Similarities in the Amino Acid Sequence of Two Proteins" (1970) J. Mol. Biol. vol. 48, pp. 443–453.

Pearson, W. et al., "Improved tools for biological sequence comparison" (1988) Proc. Natl. Acad. Sci. USA vol. 85, pp. 2444–2448.

Russell, R. et al., "Engineering thermostability: lessons from thermophilic proteins" (1995) Curr. Opin. In Biotech. vol. 6, No. 4, pp. 370–374.

Sambrook, J. et al., "Molecular Cloning: A Labortary Manual," $2^{nd}$ ed., Cold Spring Harbor Laboratory Press, pp. 1.20–1.110, 2.4–2.125.

Schulein, Martin, "Cellulases of Trichoderma reesei," Methods in Enzymology, 160, 25, pp. 234–242, 1988.

Sheir–Neiss, G., et al. "Characterization of the secreted cellulases of Trichoderma reesei wild type and mutants during controlled fermentations," Appl. Microbiol. Biotechnol., 20:46–53, 1984.

Shizuoka Perfectural Hammamatsu Textile Industrial Research Institute Report 24:54–61 (1986).

Smith, Temple F., et al., "Comparison of Biosequences," Adv. Appl. Math. 2:482–489, 1981.

Sulzenbacher, G. et al., "The Crystal Structure of a 2–Fluorocellotrisyl Complex of the Streptomyces lividans Endoglucanase CelB2 at 1.2 ÅResolution" (1999) Biochem. vol. 38, No. 15, pp. 4826–4833.

Sulzenbacher, Gerlind, et al., "The Streptomyces lividans Family 12 Endoglucanase: Construction of the Catalytic Core, Exprssion, and X–ray Structure at 1.75 ÅResolution†‡, " Biochemistry 36 :16032–16039, 1997.

Tanner, J. et al., "Determinants of Enzyme Thermostability Observed in the Molecular Structure of Thermus aquaticus D–Glyceraldehyde–3–phosphate Dehydrogenase at 2.5 ÅResolution" (1996) Biochem. vol. 35, No. 8, pp. 2597–2609.

Ward, M. et al., "Trichoderma Reesei Cellulases and other Hydrolases" (1993) Proc. Of the Tricel Symposium vol. 8, pp. 153–158.

Watanabe, K. et al., "Multiple proline substitutions cumulatively thermstabilize Bacillus cereus ATCC7064 oligo–1, 6–glucosidase" (1994) Eur. J. Biochem. vol. 226, pp. 277–283.

Zuber, H., "Temperature adaptation of lactate dehydrogenase, Structural, functional and genetic aspects" (1990) Biohpys. Chem. 19:171–179.

* cited by examiner

Amino Acid Sequence of Mature EGIII Protein

```
QTSCDQWATFTGNGYTVSNNLWGASAGSGFGCVTAVSLSGGASWHADWQWSGGQNNVKSY   60
QNSQIAIPQKRTVNSISSMPTTASWSYSGSNIRANVAYDLFTAANPNHVTYSGDYELMIW  120
LGKYGDIGPIGSSQGTVNVGGQSWTLYYGYNGAMQVYSFVAQTNTTNYSGDVKNFFNYLR  180
DNKGYNAAGQYVLSYQFGTEPFTGSGTLNVASWTASIN                        218
```

FIGURE 1

DNA Sequence of EGIII Without Introns

```
ATGAAGTTCCTTCAAGTCCTCCCTGCCCTCATACCGGCCGCCCTGG
CCCAAACCAGCTGTGACCAGTGGGCAACCTTCACTGGCAACGGCTA
CACAGTCAGCAACAACCTTTGGGGAGCATCAGCCGGCTCTGGATTT
GGCTGCGTGACGGCGGTATCGCTCAGCGGCGGGGCCTCCTGGCACG
CAGACTGGCAGTGGTCCGGCGGCCAGAACAACGTCAAGTCGTACC
AGAACTCTCAGATTGCCATTCCCCAGAAGAGGACCGTCAACAGCAT
CAGCAGCATGCCCACCACTGCCAGCTGGAGCTACAGCGGGAGCAA
CATCCGCGCTAATGTTGCGTATGACTTGTTCACCGCAGCCAACCCG
AATCATGTCACGTACTCGGGAGACTACGAACTCATGATCTGGCTTG
GCAAATACGGCGATATTGGGCCGATTGGGTCCTCACAGGGAACAG
TCAACGTCGGTGGCCAGAGCTGGACGCTCTACTATGGCTACAACGG
AGCCATGCAAGTCTATTCCTTTGTGGCCCAGACCAACACTACCAAC
TACAGCGGAGATGTCAAGAACTTCTTCAATTATCTCCGAGACAATA
AAGGATACAACGCTGCAGGCCAATATGTTCTTAGCTACCAATTTGG
TACCGAGCCCTTCACGGGCAGTGGAACTCTGAACGTCGCATCCTGG
ACCGCATCTATCAAC
```

FIGURE 2

```
                              1                                                          60
               T._reesei      M.........KF.LQVLPALIPAALAQTS...............CDQWATFTGNG..YTV
         H._schweinitzii      M.........KF.LQVLPAILPAALAQTS...............CDQYATFSGNG..YIV
           A._aculeatus  *    M.........KAFHL.LAALAGAAVAQQAQ..............LCDQYATYTGGV..YTI
            A._kawachii  *    M.........KLSMT.LSLFAATAMGQT................MCSQYDSASSPP..YSV
           A._kawachii_2      M.........KAFHL.LAALSGAAVAQQAQ..............LCDQYATYTGGV..YTI
             A._oryzae  *     M.........KLSLA.LATLVATAFSQE................LCAQYDSASSPP..YSV
                H._grisei     M........LKSALLLGAAAVSVQSASIPTIPANLEPRQIR.SLCELYGYWSGNG..YEL
           H._insolens  *     M........LKSALLLGPAAVSVQSASIPTIPANLEPRQIR.SLCELYGYWSGNG..YEL
     Chaetomium_brasiliense   M.........KLTLVLFVSSLA......AATPLGWRERQQQVSLCGQSSSWSGNG..YQL
                F._equseti    M.........KSTLLLAGAFAPLAFAKD................LCEQYGYLSSDG..YSL
              F._javanicum_1  M.........KSAIVA.ALAGLAAASPTRLIPRGQ........FCGQWDSETAGA..YTI
              F._javanicum_2  M.........K..FFGVVSASLAATAVATPTTPTETIEKRDTTWCDAFGSLATSG..YTV
              G._roseum_Rj_1  M.........KANIVILSLFAPLAAVAQT...............LCGQYSSNTQGG..YIF
              G._roseum_Rj_2  M.........KSIISFFGLATLVAAAPSQNPTRTQPLEKRATTLCGQWDSVETGG..YTI
              G._roseum_PA_3  M.........KFQLLSLTAFAPLSLAA.................LCGQYQSQSQGG..YIF
              G._roseum_Rj_4  M.........KTGIAYLAAVLPLA.MAES...............LCDQYAYLSRDG..YNF
         Memnoniella_echinata M.........KVAAL.LVALSPLAF.AQS...............LCDQYSYYSSNG..YEF
         Emericella_desertoru M.........K..LLALSLVSLASAASAASIL.SNTFTRRSD.FCGQWDTATVGN..FIV
          Actinomycete_11AG8  MRS......HPRS..ATM.TVLVVLASLGALLTAAAPAQANQQICDRYGTTTIQD.RYVV
          S._lividans_CelB  * MRTLRPQARAPRGLLAALGAVLAAFALVSSLVTAAAPAQADTTICEPFGTTTIQG.RYVV
          Rhodothermus_marinus* MNVMR..AVLVLSLLLLFGCDWL.FPDGDNGKEPEPEPEPTVELCGRWDARDVAGGRYRV
              Erwinia_carot * MQTVNTQPHRIFRVLLPAVFSSLLLSSLTVSAASSSNDADKLYF.........GNNKYYL 61                                                         120
               T._reesei      SNNLWGASAGSGF..GCV.TAVSLSGG.ASWHADWQWSGGQNNVKSYQNS..........
         H._schweinitzii      SNNLWGASAGSGF..GCV.TSVSLNGA.ASWHADWQWSGGQNNVKSYQNV..........
           A._aculeatus  *    NNNLWGKDAGSG..SQCTTVNSASSAG.TSWSTKWNWSGGENSVKSYANS..........
            A._kawachii  *    NQNLWGEYQGTG..SQCVYVDKLSSSG.ASWHTKWTWSGGEGTVKSYSNS..........
           A._kawachii_2      NNNLWGKDAGSG..SQCTTVNSASSAG.TSWSTKWNWSGGENSVKSYANS..........
             A._oryzae  *     NNNLWGQDSGTGFTSQCVYVDNLSSSG.AAWHTTWTWNGGEGSVKSYSNS..........
                H._grisei     LNNLWGKDTATS.GWQCTYLDGTNNGG.IQWSTAWEWQGAPDNVKSYPYV..........
           H._insolens  *     LNNLWGKDTATS.GWQCTYLDGTNNGG.IQWSTAWEWQGAPDNVKSYPYV..........
     Chaetomium_brasiliense   NNNLWGQSRATS.GSQCTYLDSSSNSG.IHWHTTWTWEGGEGEVKSYAYS..........
                F._equseti    NNNVWGKDSGTGD..QCTHVNWNNANG.AGWDVEWNWSGGKDNVKSYPNS..........
              F._javanicum_1  YNNLWGKDNAES.GEQCTTNSGEQSDGSIAWSVEWSWTGGQGQVKSYPNA..........
              F._javanicum_2  YHNNWGKGDATS.GSQCTTFTSVSNNNFV.WSTSWTWAGGAGKVKSYSNV..........
              G._roseum_Rj_1  NNNMWGMGSGSGS..QCTYVDKVWAEG.VAWHTDWSWSGGDNNVKSYPYS..........
              G._roseum_Rj_2  YNNLWGQDNG.S.GSQCLTVEGV.TDGLAAWSSTWSWSGGSSSVKSYSNA..........
              G._roseum_PA_3  NNNKWGQGSGSGS..QCLTIDKTWDSN.VAFHADWSWSGGTNNVKSYPNA..........
              G._roseum_Rj_4  NNNEWGAATGTGD..QCTYVDSTSSGG.VSWHSDWTWSGSESEIKSYPYS..........
         Memnoniella_echinata NNNMWGRNSGQGN..QCTYVDYSSPNG.VGWRVNWNWSGGDNNVKSYPYS..........
         Emericella_desertoru YNNLWGQDNADS.GSQ..TGVDSANGNSISWHTTWSWSGGSSVKSYANA..........
          Actinomycete_11AG8  QNNRWGTSAT.....QCINVT..GNGFEITQADGS..VPTNGAPKSYPSVYDGCHYG...
          S._lividans_CelB  * QNNRWGSTAP.....QCVTAT..DTGFRVTQADGS..APTNGAPKSYPSVFNGCHYT...
          Rhodothermus_marinus* INNVWGAETA.....QCIEVGLETGNFTITRADHD..NGNNVA..AYPAIYFGCHWAPAR
              Erwinia_carot * FNNVWGKDEIKGWQQTIFYNSPISMG....WN..WHWPSSTHSVKAYPSLVSGWHWTAG.

121                                                        180
               T._reesei      .QIAIP.QKRTVNSISSMPTTASW...SYSGSNIRANVAYDL.FTAANPNHVTYSGDYEL
         H._schweinitzii      .QINIP.QKRTVNSIGSMPTTASW...SYSGSDIRANVAYDL.FTAANPNHVTYSGDYEL
           A._aculeatus  *    .GLTF..NKKLVSQISQIPTTARW.S...YDNTGIRADVAYDL.FTAADINHVTWSGDYEL
            A._kawachii  *    .GLTF..DKKLVSDVSSIPTSVTW.SQD..DTNVQADVSYDL.FTAANADHATSSGDYEL
           A._kawachii_2      .GLSF..NKKLVSQISHIPTAARW.S...YDNTCIRRGRAYDL.FTAADINHVTWSGDYEL
             A._oryzae  *     .AVTF..DKKLVSDVQSIPTDVEW.SQDFTNTNVNADVAYDL.FTAADQNHVTYSGDYEL
                H._grisei     .GKQIQRGRK.ISDINSMRTSVSW...TYDRTDIRANVAYDL.FTARDPDHPNWGGDYEL
           H._insolens  *     .GKQIQRGRK.ISDINSMRTSVSW...TYDRTDIRANVAYDV.FTARDPDHPNWGGDYEL
     Chaetomium_brasiliense   .GRQVSTGLT.IASIDSMQTSVSW...EYNTTDIQANVAYDI.FTAEDPDHEHSSGDYEL
                F._equseti    .ALLIGEDKKTISSITNMQSTAEW...KYSGDNLRADVAYDL.FTAADPNHETSSGEYEL
              F._javanicum_1  .VVEI..EKKTLGEVSSIPSA..W.DWTYTGNGIIANVAYDL.FTSSTESGDA...EYEF
              F._javanicum_2  .ALEK..INKKISDIKSVSTR...W.IWRYTGTKMIANVSYDL.WFAPTASSNN...AYEI
              G._roseum_Rj_1  .GRELGT.KRIVSSIKSISSGADW...DYTGSNLRANAAYDI.FTSANPNHATSSGDYEV
              G._roseum_Rj_2  .VLSA..EAARISAISSIPSK..W.EWSYTGTDIVANVAYDL.FSNTDCGDTP...EYEI
              G._roseum_PA_3  .GLEFSR.GKKVSSIGTINGGADW...DYSGSNIRANVAYDI.FTSADPNHVTSSGDYEL
              G._roseum_Rj_4  .GLDLPE.KKIVTSIGSISTGAEW...SYSGSDIRADVAYDT.FTAADPNHATSSGDYEV
         Memnoniella_echinata .GRQLPT.KRIVSWIGSLPTTVSW...NYQGNNLRANVAYDL.FTAANPNHPNSSGDYEL
         Emericella_desertoru .AYQF..TSTKLNSLSSSIPTS..W.KWQYSTTDIVANVAYDL.FTSSSAGGDS...EYEI
```

FIGURE 3A

```
       Actinomycete_11AG8  ...NCAPRTTLPMRISSIGSAPSSVSYRYTGNGVY.NAAYDIWLDPTPRTNGVNR..TEI
        S._lividans_CelB__*  ...NCSPGTDLPVRLDTVSAAPSSISYGFVDGAVY.NASYDIWLDPTARTDGVNQ..TEI
      Rhodothermus_marinus__* AIRDCAARAGAVRRAHELDVTP.......ITTGRW.NAAYDIWFSPVTNSGNGYSGGAEL
            Erwinia_carot__*  ....YTENSGLPIQLSSNKSITSNVTYSIKATGTY.NAAYDIWFHTTDKANWDSSPTDEL 181                                                        240
                  T._reesei  MIWLGKYGDIGPIGSS....QGTVNVGGQSWTLYYGYNGAMQV......YSFVAQT.NTT
            H._schweinitzii  MIWLGKYGDIGPIGSS....QGTVNVGGQTWTLYYGYNGAMQV......YSFVAQS.NTT
              A._aculeatus__*  MIWLARYGGVQPIGSQ....IATATVDGQTWELWYG......ANGSQKTYSFVAPT.PIT
               A._kawachii__*  MIWLARYGSVQPIGKQ....IATATVGGKSWEVW..YGTSTQAGAEQKTYSFVAGS.PIN
               A._kawachii_2  MIWLARYGGVQPLGSQ....IATATVEGQTWELWYG......VNGAQKTYSFVAAN.PIT
                A._oryzae__*  MIWLARYGTIQPIGTQ....IDTATVEGHTWELWFTYGTTIQAGAEQKTYSFVSAT.PIN
                  H._grisei  MIWLARYGGIYPIGTF....HSQVNLAGRTWDLWTGYNGNMRV......YSFLPPSGDIR
              H._insolens__*  MIWLARYGGIYPIGTF....HSQVNLAGRTWDLWTGYNGNMRV......YSFLPPSGDIR
        Chaetomium_brasiliense MIWLARYNNVSPIGSS....VATATVGGDTWDLFAGANGDMEV......YSFVAENT.MN
                 F._equseti  MVWLARIGGVQPIGSL....QTSVTIEGHTWELWVGMNGSMKV......FSFVAPT.PVN
               F._javanicum_1 MIWLSALGGAGPISNDGSP.VATAELAGTSWKLYQGKNNQMTV......FSFVAESDV.N
               F._javanicum_2 MIWVGAYGGALPISTPGKGVIDRPTLAGIPWDVYKGPNGDVTV......ISFVASSNQ.G
                G._roseum_Rj_1 MIWLANLGGLTPIGSP....IGTVKAAGRDWELWDGYNGAMRV......YSFVAPS.QLN
                G._roseum_Rj_2 MIWLSALGGAGPISSTGSS.IATVTIAGASWNLWQGQNNQMAV......FSFVAESDQ.K
                G._roseum_PA_3 MIWLGKLGDIYPIGNS....IGRVKAANREWDLHVGYNGAMKV......FSFVAPS.PVT
                G._roseum_Rj_4 MIWLANLGGLTPIGSP....IGTVKAAGRDWELWDGYNGAMRV......YSFVAPS.QLN
          Memnoniella_echinata MIWLGRLGNVYPIGNQ....VATVNIAGQQWNLYYGYNGAMQV......YSFVSPN.QLN
          Emericella_desertoru MIWLAALGGAGPISSTGSS.IATVTLGGVTWSLYSGPNGSMQV......YSFVASSTT.E
       Actinomycete_11AG8  MIWFNRVGPVQPIGSP....VGTASVGGRTWEVWSGGNGSNDVI......SFLAPSA.IS
        S._lividans_CelB__*  MIWFNRVGPIQPIGSP....VGTASVGGRTWEVWSGGNGSNDVL......SFVAPSA.IS
      Rhodothermus_marinus__* MIWLNWNGGVMPGGSR....VATVELAGATWEVWYADWDWNYIA......YRRTTPT.TS
            Erwinia_carot__*  MIWLNDTNA.....GPAGDYIETVFLGDSSWNVFKGWINADN.GGGWNVFSFVHTSGTNS 241                                                        300
                  T._reesei  NYSGDVKNFFNYLRDNKGYNAAGQYV..LSYQFGTEPF..TGSGT.LNVASWTASI.N..
            H._schweinitzii  SYSGDVKNFFNYLRDNKGYNAGGQYV..LSYQFGTEPF..TGSGT.LNVASWTASI.N..
              A._aculeatus__*  SFQGDVNDFFKYLTQNHGFPASSQYLI..TLQFGTEPF..TGGPATLSVSNWSASVQQAG
               A._kawachii__*  SWSGDIKDFFNYLTQNQGFPASSQHLI..TLQCGTEPF..TGGPATFTVDNWTASVN...
               A._kawachii_2  SFQGDINDFFKYLTQNHGFPASSQYLIILALQFGTEPF..TGGPATLNVADWSASVQ...
                A._oryzae__*  TFGGDIKKFFDYITSKHSFPASAQYLI..NMQFGTEPFFTTGGPVTFTVPNWTASVN...
                  H._grisei  DFSCDIKDFFNYLERNHGYPAREQNLIV..YQVGTECF..TGGPARFTCRDFRADL....
              H._insolens__*  DFSCDIKDFFNYLERNHGYPAREQNLIV..YQVGTECF..TGGPARFTCRDFRADL....
        Chaetomium_brasiliense SFSGDVKDFFFDYLEQNVGFPVDDQYLLV..FELGSEAF..TGGPATLSVSQFSANI....
                 F._equseti  NFNADIKQFWDYLTKSQNFPADNQYL..LTFQFGTEPF..TGDNAKFTVTNFNAHLK...
               F._javanicum_1 NFCGDLADFTDYLVDNHGVSSSQ...ILQSVGAGTEPF..EGTNAVFTTNNYHADVE...
               F._javanicum_2 NFQADLKEFLNYLTSKQGLPSNY...VATSFQAGTEPF..EGTNAVLKTSAYTISVN...
                G._roseum_Rj_1 SFDGEIMDFFYVVKDMRGFPADSQHL..LTVQFGTEPI..SGSGAKFSVSHWSAKLG...
                G._roseum_Rj_2 SFSGDLNDFIQYLVDSQGYSGSQ...CLYSIGAGTEPF..TGTDAEFITTGYSVSVSAGD
                G._roseum_PA_3 RFDGNIMDFFYVMRDMQGYPMDKQYL..LSLQFGTEPF..TGSNAKFSCWYFGAKIK...
                G._roseum_Rj_4 SFDGEIMDFFYVVKDMRGFPADSQHL..LTVQFGTEPI..SGSGAKFSVSHWSAKLG...
          Memnoniella_echinata YFSGNVKDFFTYLQYNRAYPADSQYL..ITYQFGTEPF..TGQNAVFTVSNWSAQQNN..
          Emericella_desertoru SFSADLMDFINYLAENQGLSSSQ...YLTHVQAGTEPF..TGTDATLTVSSYSVSVS...
       Actinomycete_11AG8  SWSFDVKDFVD.QAVSHGLATPDWYLT..SIQAGFEPW...EGGTGLAVNSFSSAVNAG.
        S._lividans_CelB__*  GWSFDVMDFVR.ATVARGLAENDWYLT..SVQAGFEPW...QNGAGLAVNSFSSTVETGT
      Rhodothermus_marinus__* VSELDLKAFID.DAVARGYIRPEWYLH..AVETGFELW...EGGAGLRTADFSVTVQ...
            Erwinia_carot__*  A.SLNIRHFTDYLVQTKQWMSDEKYIS..SVEFGTEIF...GGDGQIDITEWRVDVK...

301                                                        360
                  T._reesei  ............................................................
            H._schweinitzii  ............................................................
              A._aculeatus__*  F........................................EPWQNGAGLAVNSF....
               A._kawachii__*  ............................................................
               A._kawachii_2  ............................................................
                A._oryzae__*  ............................................................
                  H._grisei  .........................................W................
              H._insolens__*  .........................................W................
        Chaetomium_brasiliense .........................................A................
                 F._equseti  ............................................................
               F._javanicum_1 ............................................................
               F._javanicum_2 ............................................................
                G._roseum_Rj_1 ............................................................
                G._roseum_Rj_2 SGCDETTTSSQAQSSTVETSTATQPQS...SSTVVPTVTLS.QPSNESTTTPVQSQ....
                G._roseum_PA_3 ............................................................
                G._roseum_Rj_4 ............................................................
          Memnoniella_echinata ............................................................
          Emericella_desertoru ............................................................
       Actinomycete_11AG8  ..GGNGGTPGTPAACQVSYSTHTWPGGFTVDTTITNTGSTPVDGWELDFTLPAGHTVTSA
        S._lividans_CelB__*  PGGTDPGDPGGPSACAVSYGTNVWQDGFTADVTVTNTGTAPVDGWQLAFTLPSGQRITNA
      Rhodothermus_marinus__* ............................................................
```

FIGURE 3B

```
                                        361
              419
              T._reesei            ................................................
         H._schweinitzii           ................................................
           A._aculeatus__*         ......SSTV......................................
           A._kawachii__*          ................................................
           A._kawachii_2           ................................................
            A._oryzae__*           ................................................
              H._grisei            ................................................
           H._insolens__*          ................................................
     Chaetomium_brasiliense        ................................................
              F._equseti           ................................................
           F._javanicum_1          ...............................................Y
           F._javanicum_2          ................................................
            G._roseum_Rj_1         ................................................
            G._roseum_Rj_2         ......PSSVETTPTAQPQSSSVQTTTTAQA....QPTSGTGCSRRRKRR......AVV
            G._roseum_PA_3         ................................................
            G._roseum_Rj_4         ................................................
         Memnoniella_echinata      ................................................
         Emericella_desertoru      ................................................
           Actinomycete_11AG8      WNALISPASGAVTARSTGSNGRIAANGGTQSFGFQGTSSGTGFNAPAGGRLNGTSCTVR
          S._lividans_CelB__*      WNASLTPSSGSVTATGASHNARIAP.GGSLSFGFQGTYGGA.FAEPTGFRLNGTACTTV
        Rhodothermus_marinus__*    ................................................
            Erwinia_carot___*      ................................................
```

Erwinia_carot___* (top row): ................................................

FIGURE 3C

MUTANT EGIII CELLULASE, DNA ENCODING SUCH EGIII COMPOSITIONS AND METHODS FOR OBTAINING SAME

CROSS-REFERENCE TO RELATED APPLICATIONS

This Application is a Continuation-in-Part of U.S. Ser. No. 09/146,770, filed Sep. 3, 1998, now U.S. Pat. No. 6,187,732, which is incorporated by reference in its entirety. This Application is related to concurrently filed applications, all of which were filed on Aug. 4, 2000 and are incorporated by reference in their entirety.

GOVERNMENT-SPONSORED RESEARCH AND DEVELOPMENT

Not applicable.

BACKGROUND OF THE INVENTION

Cellulases are enzymes that are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), TIBTECH 5, 255–261); and are known to be produced by a large number of bacteria, yeasts and fungi.

Although cellulases are used to degrade wood pulp and animal feed, cellulases are primarily used in the treatment of textiles, e.g., in detergent compositions for assisting in the removal of dirt or grayish cast (see e.g., Great Britain Application Nos. 2,075,028, 2,095,275 and 2,094,826) or in the treatment of textiles prior to sale to improve the feel and appearance of the textile. Thus, Great Britain Application No. 1,358,599 illustrates the use of cellulase in detergents to reduce the harshness of cotton containing fabrics.

Cellulases have also been used in the treatment of textiles to recondition used fabrics by making their colors more vibrant (see e.g., The Shizuoka Prefectural Hammamatsu Textile Industrial Research Institute Report 24:54–61 (1986)). Repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Because of its effectiveness in many industrial processes, there has been a trend in the field to search for specific cellulase compositions or components that have particularly effective performance profiles with respect to one or more specific applications. As possible sources of cellulases, practitioners have focused on fungi and bacteria. For example, cellulase produced by certain fungi such as Trichoderma spp. (especially Trichoderma reesei) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes (see, Wood et al., "Methods in Enzymology", 160, 25, pages 234, et seq. (1988). U.S. Pat. No. 5,475,101 (Ward et al.) discloses the purification and molecular cloning of one particularly useful enzyme called endoglucanase III (EGIII) which is derived from Trichoderma reesei.

PCT Publication No. WO 94/14953 discloses endoglucanases that are encoded by a nucleic acid that comprises any one of a series of DNA sequences, each having 20 nucleotides.

Ooi, et al., Curr. Genet. 18:217–222 (1990) disclose the cDNA sequence coding for endoglucanase F1-CMC produced by Aspergillus aculeatus that contains the amino acid strings NNLWG, ELMIW and GTEPFT. Sakamoto, et al., Curr. Genet. 27:435–439 (1995) discloses the cDNA sequence encoding the endoglucanase CMCase-1 From Aspergillus kawachii IFO 4308 which contains the amino acid strings ELMTW and GTEPFT. Ward, et al., discloses the sequence of EGIII having the amino acid strings NNLWG, ELMIW and GTEPFT. Additionally, two cellulase sequences, one from Erwinia carotovara and Rhodothermus marinus are disclosed in Saarilahti, et al., Gene 90:9–14 (1990) and Hreggvidsson, et al., Appl. Environ. Microb. 62:3047–3049 (1996) that contain the amino acid string ELMIW.

Despite knowledge in the art related to many cellulase compositions having applications in some or all of the above areas, there is a continued need for new cellulase compositions which have improved stability under conditions present in applications for which cellulases are useful, e.g., household and laundry detergents and textile treatment compositions.

SUMMARY OF THE INVENTION

A variant EGIII cellulase is provided wherein the variant comprises a substitution at a residue that is sensitive to surfactant and/or temperature stress and is derived from T. reesei EGIII cellulase. In a preferred embodiment, the variant comprises a substitution or deletion at a position corresponding to one or more of residues W7, T11, T16, A35, S39, G41, S63, A66, S77, N91, S143, T163, N167 and/or, A188. In a more preferred embodiment, the variant comprises a substitution at a position corresponding to one or more of residues W7Y, T11S, T16I, A35S, S39N, G41A, S63V, A66N, S77G, N91D, S143T, T163S, N167S and/or, A188G.

In another embodiment of the invention, a DNA encoding the variant EGIII cellulase is provided. In a preferred aspect of this embodiment, the DNA is in a vector. In another aspect of this embodiment, the vector is used to transform a host cell.

In yet another embodiment, a method of producing a variant EGIII cellulase having improved stability and/or performance is provided. The method comprises the steps of culturing a host cell in a suitable culture medium under suitable conditions to produce cellulase and obtaining the produced cellulase. In another embodiment a detergent composition comprising a surfactant and a variant EGIII cellulase is provided, wherein the variant EGIII cellulase comprises a substitution at residue sensitive to surfactant and/or temperature. In a preferred embodiment, the variant comprises a substitution or deletion at a position corresponding to one or more of residues W7, T11, T16, A35, S39, G41, S63, A66, S77, N91, S143, T163, N167 and/or, A 188G. In a more preferred embodiment, the variant EGIII cellulase comprises a substitution at a position corresponding to one or more of residues W7Y, T11S, T16I, A35S, S39N, G41A, S63V, A66N, S77G, N91D, S143T, T163S, N167S and/or, A188G. In another aspect of this embodiment, the detergent is a laundry or a dish detergent.

In another embodiment of this invention, the variant EGIII cellulase is used in the treatment of a cellulose-containing textile, preferably to stone wash indigo dyed denim. In another embodiment, the variant is used as a feed additive. In yet another embodiment, the variant is used in the treatment of wood pulp. In still another embodiment, the variant is used in the reduction of biomass to glucose.

BRIEF DESCRIPTION OF THE DRAWINGS

FIG. 1 illustrates the amino acid sequence of EGIII from *Trichoderma reesei*.

FIG. 2 illustrates the DNA sequence of EGIII from *Trichoderma reesei* without introns.

FIG. 3 is a schematic showing the alignment of amino acids in EGIII and EGIII-like cellulases.

DETAILED DESCRIPTION OF THE INVENTION

Applicants have isolated a novel cellulase from *Hypocrea schweinitzii* that has significant homology to EGIII from *Trichoderma reesei*. Analysis of this cellulase has resulted in the discovery that substantial differences exist in terms of performance between the two cellulases, despite the significant homology. In fact, the homologous enzyme has significantly diminished performance under conditions of thermal stress or in the presence of surfactants. This discovery is particularly interesting as EGIII differs from its *Hypocrea schweinitzii* homolog in only 14 positions indicating that these 14 positions lie in portions or areas of the protein that have a significant impact on the stability and/or performance of EGIII. Thus, Applicants discovered that by optimizing residues in EGIII at one or more of the 14 different positions or spatially near them, it is possible to optimize the performance of EGIII.

Accordingly, the present invention relates to a variant EGIII cellulase having improved performance in the presence of, e.g., surfactant and/or thermal mediated stress. The variant is characterized by replacement of one or more residues identified herein as being critical for stability and/or performance with a residue that confers improved stability and/or performance to the enzyme. Preferably, but not necessarily, the sensitive residue is replaced with a residue that has improved oxidative, alkaline or thermal stability compared to the wild type (*T. reesei* EGIII) residue at that position. Suitable substitutions may be any substitution that modifies stability, particularly preferred substitutions being those which provide improved stability and most preferred substitutions being those which provide conservative modifications in terms of charge, polarity and/or size. As a non-limiting example, substitutions which are particularly of value include substitutions wherein leucine is modified to an isoleucine, isoleucine is modified to a leucine, tryptophan is modified to a tyrosine, threonine is modified to an asparagine, alanine is modified to a glycine, serine is modified to an asparagine, glycine is modified to a proline and asparagine is modified to a threonine.

Definitions

Within the specification, certain terms are disclosed which are defined below so as to clarify the nature of the claimed invention.

"Cellulase" is a well-classified category of enzymes in the art and includes enzymes capable of hydrolyzing cellulose polymers to shorter cello-oligosaccharide oligomers, cellobiose and/or glucose. Common examples of cellulase enzymes include exo-cellobiohydrolases and endoglucanases and are obtainable from many species of cellulolytic organisms, particularly including fungi and bacteria.

"EGIII cellulase" refers to the endoglucanase component described in U.S. Pat. No. 5,475,101 and *Proceedings on the Second TRICEL Symposium on Trichoderma Reesei Cellulases And Other Hydrolases*, Suominen & Reinikainen eds., Espoo Finland (1993), pp. 153–158 (Foundation for Biotechnical and Industrial Fermentation Research, Vol. 8). As discussed therein, EGIII is derived from *Trichoderma reesei* (*reesei*) and is characterized by a pH optimum of about 5.8, an isoelectric point (pI) of about 7.4 and a molecular weight of about 25 kD. The enzyme commonly referred to as EGIII from *Trichoderma reesei* has been previously preferred to in the literature by the nomenclature EGIII by some authors, but that enzyme differs substantially from the enzyme defined herein as EGIII in terms of molecular weight, pI and pH optimum.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g., lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

A residue in an EGIII homolog from *H. schweinitzii* which is "corresponding" or "equivalent" to a residue present in EGIII means a residue which exists in an equivalent position to that in EGIII, as indicated by primary sequence homology, tertiary structural homology (as shown by, e.g., crystal structure or computer modeling) or functional equivalence.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of a EGIII homolog from *H. schweinitzii* and *T. reesei* EGIII (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the EGIII homolog in question to the *T. reesei* EGIII. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *T. reesei* EGIII are defined as those amino acids of a cellulase which may adopt a conformation such that they either alter, modify or contribute to protein structure, substrate binding or catalysis in a manner defined and attributed to a specific residue of the *T. reesei* EGIII. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.1 3nm of the corresponding side chain atoms of *T. reesei* EGIII. The crystal structure of *T. reesei* EGIII is presented The Protein Society, Fourteenth Symposium. San Diego, Calif. Aug. 5–9, 2000, the disclosure of which is incorporated by reference in its entirety. The coordinates of CelB of *Streptomyces lividans*, a homologous member of the Family 12 glycosyl hydrolases is provided in Sulzenbacher, et al., *Biochemistry* 36:6032 (1997) and in Sulzenbacher, et al., *Biochemistry* 38:4826 (1999).

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Detergent composition" means a mixture that is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, U.S. Pat. No. 5,290,474 and EP Publication No. 271 004, incorporated herein by reference.

"DNA vector" means a nucleotide sequence that comprises one or more DNA fragments or DNA variant fragments encoding an EGIII or variants described above, which can be used, upon transformation into an appropriate host cell, to cause expression of the EGIII.

"Expression vector" means a DNA construct comprising a DNA sequence that which is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences that control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* (*reesei*) is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors that serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2 μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook, et al., *Molecular Cloning: A Laboratory Manual, Second Edition*, Cold Spring Harbor Press (1989). Often, such expression vectors including the DNA sequences of the invention are transformed into a unicellular host by direct insertion into the genome of a particular species through an integration event (see e.g., Bennett & Lasure, MORE GENE MANIPULATIONS IN FUNGI, Academic Press, San Diego, pp. 70–76 (1991) and articles cited therein describing targeted genomic insertion in fungal hosts, incorporated herein by reference).

"Functionally attached to" means that a regulatory region, such as a promoter, terminator, secretion signal or enhancer region is attached to a structural gene and controls the expression of that gene.

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma reesei* (*reesei*), *Saccharomyces cerevisiae* or *Aspergillus niger*. Host cells are transformed or transfected with vectors constructed using recombinant DNA techniques. Such transformed host cells are capable of both replicating vectors encoding swollenin and its variants (mutants) or expressing the desired peptide product. In a preferred embodiment according to the present invention, "host cell" means both the cells and protoplasts created from the cells of *Trichoderma sp*.

"Stonewashing" means the treatment of cellulose containing fabric with a cellulase solution under agitating and cascading conditions, e. g., in a rotary drum washing machine, to impart a "stonewashed" appearance to the denim. The cellulase solution according to the instant invention will functionally replace the use of stones in such art-recognized methods, either completely or partially. Methods for imparting a stonewashed appearance to denim are described in U.S. Pat. No. 4,832,864, which is incorporated herein by reference in its entirety. Generally, stonewashing techniques have been applied to indigo dyed cotton denim.

"Stonewashing composition" means a formulation for use in stonewashing cellulose containing fabrics. Stonewashing compositions are used to modify cellulose-containing fabrics prior to presentation for consumer sale, i.e., during the manufacturing process. In contrast, detergent compositions are intended for the cleaning of soiled garments.

"Signal sequence" means a sequence of amino acids bound to the N-terminal portion of a protein that facilitates the secretion of the mature form of the protein outside of the cell. This definition of a signal sequence is a functional one. The mature form of the extracellular protein lacks the signal sequence that is cleaved off during the secretion process.

"Surfactant" means any compound generally recognized in the art as having surface-active qualities. Thus, for example, surfactants comprise anionic, cationic and non-ionic surfactants such as those commonly found in detergents. Cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Examples of cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like. Examples of surfactants for use in this invention are disclosed in British Patent Application No. 2 094 826 A, the disclosure of which is incorporated herein by reference. Mixtures of such surfactants can also be used.

"Variant" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or, at one or more sites in the amino acid sequence, or insertion of one or more amino acids at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the variant enzyme. The variant of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. For example, an EGIII variant may have an increased pH optimum or increased temperature or oxidative stability but will retain cellulolytic activity. It is contemplated that variants according to the present invention may be derived from a DNA fragment encoding a cellulase derivative wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained.

Alignment of Amino Acid Sequences

The variant EGIIIs of this invention have amino acid sequences that are derived from the amino acid sequence of a precursor EGIII. The amino acid sequence of the EGIII variant differs from the precursor EGIII amino acid sequence by the substitution, deletion or insertion of one or more amino acids of the precursor amino acid sequence. In a preferred embodiment, the precursor EGIII is *Trichoderma reesei* EGIII. The mature amino acid sequence of *T. reesei* EGIII is shown in FIG. 1. Thus, this invention is directed to EGIII variants that contain amino acid residues at positions that are equivalent to the particular identified residue in *T. reesei* EGIII as well as at least one residue that is equivalent to an identified residue in a *H. schweinitzii* EGIII homolog. A residue (amino acid) of an EGIII homolog is equivalent to a residue of *Trichoderma reesei* EGIII if it is either homologous (i.e., corresponding in position in either primary or tertiary structure) or is functionally analogous to a specific residue or portion of that residue in *Trichoderma reesei* EGIII (i.e., having the same or similar functional capacity to combine, react, or interact chemically or structurally). As used herein, numbering is intended to correspond to that of the mature EGIII amino acid sequence as illustrated in FIG. 2. In addition to locations within the precursor EGIII, specific residues in the precursor EGIII corresponding to the amino acid positions that are responsible for instability when the precursor EGIII is under thermal or surfactant stress are identified herein for substitution or deletion. The amino acid position number (e.g., +35) refers to the number assigned to the mature *Trichoderma reesei* EGIII sequence presented in FIG. 1.

The precursor EGIII of this invention include naturally occurring cellulases and recombinant cellulases (as defined herein). It is intended that the DNA that encodes the precursor EGIII is modified rather than manipulation of the precursor cellulase enzyme per se. Suitable methods for such manipulation of the precursor DNA sequence include methods disclosed herein and in commonly owned U.S. Pat. Nos. 4,760,025 and 5,185,258.

Alignment of amino acid sequences to determine homology is preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information (http:H/www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

In addition to substitution of an amino acid residue present in *H. schweinitzii*, other residues can be substituted into EGIII at thermal and/or surfactant sensitive residues. For example, in *H. schweinitzii*-like EGIII, a serine is at position 35 When this residue is substituted for the alanine present in *T. reesei* EGIII, thermal stability decreases by about 4° C. However, if a valine is substituted for the alanine, the Tm increases by about 6.5° C. Thus, position 35 is a thermally sensitive site and stability can be increased or decreased depending on the substitution.

In addition to modulating thermal and/or surfactant stability, amino acid substitutions can affect other characteristics of *T. reesei* EGIII, e.g., substrate binding, inhibitor binding, solubility and performance under pH stress. For example, substitution of a tyrosine for a tryptophan at position 7 decreases the Tm of an EGIII variant by about 1° C. However, this substitution inhibits the binding of cellobiose to the variant. Cellobiose is an inhibitor of *T. reesei* EGIII. Thus, the variant, even though it may be less thermally stable than *T. reesei* EGIII, may perform better in applications where cellobiose is present, e.g., biomass conversion.

Additional specific strategies for modifying stability of EGIII cellulases are provided below:

(1) Increasing the entropy of main-chain unfolding may introduce stability to the enzyme. For example, the introduction of proline residues into position 2 of reverse turns at the N-termini of α-helices and in loop structures may significantly stabilize the protein by increasing the entropy of the unfolding (see, e.g., Watanabe, et al., *Eur. J. Biochem.* 226:277–283 (1994)). Similarly, glycine residues have no β-carbon, and thus have considerably greater backbone conformational freedom than many other residues. This may lead to high flexibility with resultant weak stability. Replacement of glycines preferably with alanines, may reduce the flexibility and improve stability. Additionally, by shortening external loops it may be possible to improve stability. It has been observed that hyperthermophile produced proteins have shorter external loops than their mesophilic homologues (see, e.g., Russel, et al., *Current Opinions in Biotechnology* 6:370–374 (1995)). The introduction of disulfide bonds may also be effective to stabilize distinct tertiary structures in relation to each other. Thus, the introduction of cysteines at residues accessible to existing cysteines or the introduction of pairs of cysteines that could form disulfide bonds would alter the stability of an EGIII variant.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, *Ann. Rev. Biochem.* 62:139–160 (1993); Burley, et al., *Science* 229:23–29 (1985); Zuber, *Biophys. Chem.* 29:171–179 (1988); Kellis, et al., *Nature* 333:784–786 (1988)). It is known that multimeric proteins from thermophiles often have more hydrophobic sub-unit interfaces with greater surface complementarity than their mesophilic counterparts (Russel, et al., supra). This principle is believed to be applicable to domain interfaces of monomeric proteins. Specific substitutions that may improve stability by increasing hydrophobicity include lysine to arginine, serine to alanine and threonine to alanine (Russel, et al., supra). Modification by substitution to alanine or proline may increase side-chain size with resultant reduction in cavities, better packing and increased hydrophobicity. Substitutions to reduce the size of the cavity, increase hydrophobicity and improve the complementarity the interfaces between the domains of EGIII may improve stability of the enzyme. Specifically, modification of the specific residue at these positions with a different residue selected from any of phenylalanine, tryptophan, tyrosine, leucine and isoleucine may improve performance.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson, et al., *Science* 255:178–183 (1992)). Similarly, neutralizing partial negative charges on helix C-terminus with positive charge may improve stability. Removing positive charge from interacting with peptide N-terminus in β-turns should be effective in conferring tertiary structure stability. Substitution with a non-positively charged residue could remove an unfavorable positive charge from interacting with an amide nitrogen present in a turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner, et al., *Biochemistry* 35:2597–2609). Substitution with aspartic acid, asparagine, glutamnic acid or glutarnine may introduce a hydrogen bond with a backbone amide. Substitution with arginine may improve a salt bridge and introduce an H-bond into a backbone carbonyl.

(5) Avoiding thermolabile residues in general may increase thermal stability. For example, asparagine and glutamine are susceptible to deamidation and cysteine is susceptible to oxidation at high temperatures. Reducing the number of these residues in sensitive positions may result in improved thermostability (Russel, et al., supra). Substitution or deletion by any residue other than glutamine or cysteine may increase stability by avoidance of a thermolabile residue.

(6) Stabilization or destabilization of binding of a ligand that confers modified stability to EGIII variants. For example, a component of the matrix in which the EGIII variants of this invention are used may bind to a specific surfactant/thermal sensitivity site of the EGIII variant. By modifying the site through substitution, binding of the component to the variant may be strengthened or diminished. For example, a non-aromatic residue in the binding crevice of EGIII may be substituted with phenylalanine or tyrosine to introduce aromatic side-chain stabilization where interaction of the cellulose substrate may interact favorably with the benzyl rings, increasing the stability of the EGIII variant.

(8) Increasing the electronegativity of any of the surfactant/thermal sensitivity ligands may improve stability under surfactant or thermal stress. For example, substitution with phenylalanine or tyrosine may increase the electronegativity of D residues by improving shielding from solvent, thereby improving stability.

Variant EGIII

The present invention relates to the expression, purification and/or isolation and use of variant EGIII. These enzymes are preferably prepared by recombinant methods utilizing the gene identified and isolated according to the methods described below. However, enzymes for use in the present invention may be obtained by other art-recognized means such as purification from natural isolates.

Techniques that can be used to isolate EGIII encoding DNA sequences is well known in the art and include, but are not limited to, cDNA and/or genomic library screening with a homologous DNA probe and expression screening with activity assays or antibodies against EGIII. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

After the isolation and cloning of the EGIII, other methods known in the art, such as site directed mutagenesis, are used to make the substitutions, additions or deletions that correspond to substituted amino acids in the expressed EGIII variant. Again, site directed mutagenesis and other methods of incorporating amino acid changes in expressed proteins at the DNA level can be found in Sambrook, et al. and Ausubel, et al.

After DNA sequences that encode the EGIII variants have been cloned into DNA constructs, the DNA is used to transform microorganisms. The microorganism to be transformed for the purpose of expressing a variant EGIII according to the present invention may advantageously comprise a strain derived from Trichoderma sp. Thus, a preferred mode for preparing variant EGIII cellulases according to the present invention comprises transforming a Trichoderma sp. host cell with a DNA construct comprising at least a fragment of DNA encoding a portion or all of the variant EGIII. The DNA construct will generally be functionally attached to a promoter. The transformed host cell is then grown under conditions so as to express the desired protein. Subsequently, the desired protein product is purified to substantial homogeneity.

However, it may in fact be that the best expression vehicle for a given DNA encoding a variant EGIII may differ from *T. reesei*. Thus, it may be that it will be most advantageous to express a protein in a transformation host which bears phylogenetic similarity to the source organism for the variant EGIII. Accordingly, the present description of a Trichoderma spp. expression system is provided for illustrative purposes only and as one option for expressing the variant EGIII of the invention. One of skill in the art, however, may be inclined to express the DNA encoding variant EGIII in a different host cell if appropriate and it should be understood that the source of the variant EGIII should be considered in determining the optimal expression host. For example, *Aspergillus niger* can be used as an expression host. See, WO 98/31821 for a description of transformation into *A. niger*. Additionally, the skilled worker in the field will be capable of selecting the best expression system for a particular gene through routine techniques utilizing the tools available in the art.

In one embodiment, the strain comprises *T. reesei* (*reesei*) which is a useful strain for obtaining overexpressed protein. For example, RL-P37, described by Sheir-Neiss, et al., *Appl. Microbiol. Biotechnol.* 20:46–53 (1984) is known to secrete elevated amounts of cellulase enzymes. Functional equivalents of RL-P37 include *Trichoderma reesei* (*reesei*) strain RUT-C30 (ATCC No. 56765) and strain QM9414 (ATCC No. 26921). It is contemplated that these strains would also be useful in overexpressing variant EGIII.

Where it is desired to obtain the variant EGIII in the absence of potentially detrimental native cellulolytic activity, it is useful to obtain a Trichoderma host cell strain which has had one or more cellulase genes deleted prior to introduction of a DNA construct or plasmid containing the DNA fragment encoding the variant EGIII. Such strains may be prepared by the method disclosed in U.S. Pat. No. 5,246,853 and WO 92/06209, which disclosures are hereby incorporated by reference. By expressing a variant EGIII cellulase in a host microorganism that is missing one or more cellulase genes, the identification and subsequent purification procedures are simplified. Any gene from Trichoderma sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with Trichoderma sp., the selectable marker is chosen so that the presence of the selectable marker in the transformants will not significantly affect the properties thereof. Such a selectable marker may be a gene which encodes an assayable product. For example, a functional copy of a Trichoderma sp. gene may be used which if lacking in the host strain results in the host strain displaying an auxotrophic phenotype.

In a preferred embodiment, a $pyr4^-$ -derivative strain of Trichoderma sp. is transformed with a functional pyr4 gene, which thus provides a selectable marker for transformation. A $pyr4^-$ -derivative strain may be obtained by selection of Trichoderma sp. strains that are resistant to fluoroorotic acid (FOA). The pyr4 gene encodes orotidine-5'-monophosphate decarboxylate, an enzyme required for the biosynthesis of uridine. Strains with an intact pyr4 gen grow in a medium lacking uridine but are sensitive to fluoroorotic acid. It is possible to select pyr4⁻ derivative strains that lack a functional orotidine monophosphate decarboxylase enzyme and require uridine for growth by selecting for FOA resistance. Using the FOA selection technique is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 19:359–365 (1991)). Selection of derivative strains is easily performed using the FOA resistance technique referred to above, and thus, the pyr4 gene is preferable employed as a selectable marker.

To transform pyr4⁻ Trichoderma sp. so as to be lacking in the ability to express one or more cellulase genes, a single DNA fragment comprising a disrupted or deleted cellulase gene is then isolated from the deletion plasmid and used to transform an appropriate pyr⁻ Trichoderma host. Transformant are then identified and selected based on their ability to express the pyr4 gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene that has been cloned, and thus identified, can be deleted from the genome using the above-described strategy.

As stated above, the host strains used are derivatives of Trichoderma sp. that lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers comprising Trichoderma sp. genes equivalent to the Aspergillus nidulans genes amdS, argB, trpC, niaD may be used. The corresponding recipient strain must therefore be a derivative strain such as argB⁻, trpC⁻, niaD⁻, respectively.

DNA encoding the variant EGIII cellulase is then prepared for insertion into an appropriate microorganism. According to the present invention, DNA encoding a variant EGIII cellulase comprises the DNA necessary to encode for a protein that has functional cellulolytic activity. The DNA fragment or DNA variant fragment encoding the variant EGIII cellulase or derivative may be functionally attached to a fungal promoter sequence, for example, the promoter of the cbh1 or egl1 gene.

It is also contemplated that more than one copy of DNA encoding a variant EGIII cellulase may be recombined into the strain to facilitate overexpression. The DNA encoding the variant EGIII cellulase may be prepared by the construction of an expression vector carrying the DNA encoding the cellulase. The expression vector carrying the inserted DNA fragment encoding the variant EGIII cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pTEX is such a general-purpose expression vector. Genes or part thereof can be inserted downstream of the strong cbh1 promoter.

In the vector, the DNA sequence encoding the variant EGIII cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. The signal peptide provides for extracellular production of the variant EGIII cellulase or derivatives thereof. The DNA encoding the signal sequence is preferably that which is naturally associated with the gene to be expressed, however the signal sequence from any suitable source, for example an exo-cellobiohydrolase or endoglucanase from Trichoderma, is contemplated in the present invention.

The procedures used to ligate the DNA sequences coding for the variant EGIII cellulase of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host Trichoderma sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tenderly integrated into the host chromosome.

Usually a suspension containing the Trichoderma sp. protoplasts or cells that have been subjected to a permeability treatment at a density of $10^8$ to $10^9$/mL, preferably $2\times10^8$/mL are used in transformation. A volume of 100 μL of these protoplasts or cells in an appropriate solution (e.g., 1.2 M sorbitol; 50 mM $CaCl^2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr⁺ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the variant EGIII cellulases or derivatives thereof are recovered in active form from the host cell after growth in liquid media either as a result of the appropriate post translational processing of the novel variant EGIII cellulase or derivatives thereof.

The expressed variant EGIII cellulase may be recovered from the medium by conventional techniques including separations of the cells from the medium by centrifugation, filtration, and precipitation of the proteins in the supernatant or filtrate with a salt, for example, ammonium sulfate. Additionally, chromatography procedures such as ion exchange chromatography or affinity chromatography may be used. Antibodies (polyclonal or monoclonal) may be raised against the natural purified variant EGIII cellulase, or synthetic peptides may be prepared from portions of the variant EGIII cellulase molecule and used to raise polyclonal antibodies.

Compositions Comprising the EGIII Variants of this Invention

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution that contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stone washing composition according to the present invention is the amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness of appearance of a fabric. The amount of cellulase employed is also dependent on the equipment employed, the process parameters employed (the temperature of the cellulase treatment solution, the exposure time to the celluloase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric is to be treated is added can be readily determined by the skilled artisan based on the above factors as well as the desired result. In stonewashing processes, it has generally been preferred that cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in ma concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which,: in turn, depends on the nature of the cellulase employed. The exact concentration of buffer employed will depend on several factors that the skilled artisan can readily take into account. For example, in a preferred embodiment, the buffer, as well as the buffer concentration, is selected so as to maintain the pH of the final cellulase solution within the pH range required for optimal cellulase activity. The determination of the optimal pH range of the cellulases of the invention can be ascertained according to well-known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283, which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, e.g., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature that allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1; and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all affect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, antigraying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase-protecting agent. The granule can be formulated so as to contain materials to reduce the rate of dissolution of the granule into the wash medium. Such materials and granules are disclosed in U.S. Pat. No. 5,254,283, which is incorporated herein by reference in its entirety.

The detergent compositions of this invention employ a surface-active agent, e.g., surfactant, including anionic, nonionic and ampholytic surfactants well known for their use in detergent compositions. In addition to the cellulase composition and the surfactant(s), the detergent compositions of this invention can optionally contain one or more of the following components.

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Builders

A. Divalent Sequesteing Agents.

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antireposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention is deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators may vary depending on the specific cellulase. In the presence of proteins, cobalt and its salts, magnesium and its salts, and calcium and its salts, potassium and its salts, sodium and its salts or monosaccharides such as mannose and xylose, many cellulases are activated and their deterging powers are improved remarkably.

Antioxidants

The antioxidants include, for example, tert-butylhydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzenesulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes, and the like can be used, if desired, with the detergent compositions of this invention. Such components are conventionally employed in amounts heretofore used in the art.

When a detergent base used in the present invention is in the form of a powder, it may be one that is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose-containing fabrics with detergent compositions according to the present invention, will be readily ascertainable by those of skill in the art. Accordingly, the appropriate conditions effective for treatment with the present detergents will correspond to those using similar detergent compositions that include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, e.g., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1
Temperature Stability Testing of EGIII and an EGIII Homolol From *Hypocrea Schweinitzii*

EGIII and an EGIII homolog derived from *Hypocrea schweinitzii* were tested to determine their stability under temperature stress. 0.3 mg/ml of enzyme was tested in 0.1M MOPS, at pH 7.3, 48° C. and the activity on oNPC measured and compared over time. The experiment was run two times. The natural log of the activity was plotted against time of incubation, and the rate constant for inactivation obtained from the slope of the straight line. Results for various mutants are provided in Table 1.

TABLE 1

Half Life of EGIII and a Homolog

| *Trichoderma reesei* EGIII | EGIII Homolog from *Hypocrea schweinitzii* |
|---|---|
| 20.2 | 3.40 |
| 21.2 | 3.90 |

As shown in Table 1, the half-life of EGIII from *T. reesei* is significantly greater than that of the EGIII homolog from *Hypocrea schweinitzii*.

Example 2
Wash Tests With EGIII and an EGIII Homolog From *Hypocrea Schweinitzii*

EGIII was compared to a homologous enzyme derived from from *Hypocrea schweinitzii*. The amino acid sequence of the enzyme from *Hypocrea schweinitzii* is provided in FIG. 3 in alignment with the sequence of EGIII. As shown in FIG. 3, the amino acid sequence of the two enzymes was found to be identical except for the residues in bold corresponding to positions 7, 11, 16, 35, 39, 41, 63, 66, 77, 91, 143, 163, 167, and 188.

In the wash test, three different enzyme mixtures (a) EGIII, (b) an EGIII homolog derived from *Hypocrea schweinitzii*, and (c) a combination of the two enzymes were prepared and mixed separately with a standard LAS containing granular detergent (4 g/L) in water having a hardness of 70 ppm $CaCO_3$ (2:1 Ca:Mg) at 40° C. in a Terg-o-Tometer with cotton swatches. The agitation was 125 rpm and the test was run for 2.5 hours. After the test, the swatches were removed from the Terg-o-Tometer, dried in a tumble drier and the level of pilling compared to a panel of fabrics pilled to varying extents. The EGIII-like enzyme from *Hypocrea schweinitzii* showed no depilling performance at any concentration. By contrast, EGIII showed depilling performance that increased in accordance with the enzyme concentration. The equivalent performance of EGIII spiked into the *Hypocrea schweinitzii* broth containing the EGIII-like enzyme indicated that it was not a component of the broth which prevented performance of the EGIII-like enzyme but, instead, the enzyme itself which had poor stability and performance.

This experiment illustrated that stability of the EGIII-like enzyme from *Hypocrea schweinitzii* is far inferior to EGIII. In fact, the related enzyme exhibited no activity in the LAS containing detergent whereas EGIII retained excellent activity.

Example 3
Thermal Stability of EGIII Variants

Site-directed mutagenesis was performed to incorporate amino acid substitutions in *T. reesei* EGIII. The amino acids substituted into the EGIII were those at homologous locations in the *H. schweinitzii* EGIII homolog.

PCR was performed according to well-known techniques.

TABLE 2

PCR primers

| Variant | Forward primer | Reverse Primer |
|---|---|---|
| W7Y | GCT GTG ACC AGT ACG CAA CCT TCA C | GTG AAG GTT GCG TAC TGG TCA CAG C |
| T11S/T | GGC AAC CTT CTC TGG | GGT TGT TGC TGA CGA |
| 16I | CAA CGG CTA CAT CGT CAG CAA CAA CC | TGT AGC CGT TGC CAG AGA AGG TTG CC |
| A35S | GGC TGC GTG ACG TCG GTA TCG CTC | GAG CGA TAC CGA CGT CAC GCA GCC |
| S39N | GGT ATC GCT CAA CGG CGG GGC CTC C | GGA GGC CCC GCC GTT GAG CGA TAC C |
| G41A | CGC TCA GCG GCG CGG CCT CCT GGC | GCC AGG AGG CCG CGC CGC TGA GCG |
| S63V | CGT ACC AGA ACG TTC AGA TTG CCA TTC C | GGA ATG GCA ATC TGA ACG TTC TGG TAC G |
| A66N | CTC TCA GAT TAA CAT TCC CCA GAA GAG G | CCT CTT CTG GGG AAT GTT AAT CTG AGA G |
| S77G | CGT CAA CAG CAT CGG CAG CAT GCC C | GGG CAT GCT GCC GAT GCT GTT GAC G |
| N91D | GCG GGA GCG ACA TCC GCG CTA ATG TTG C | GCA ACA TTA GCG CGG ATG TCG CTC CCG C |
| S143T | CGT CGG TGG CCA GAC CTG GAC GC | GCG TCC AGG TCT GGC CAC CGA CG |
| T163S | CCT TTG TGG CCC AGA GCA ACA CTA CC | GGT AGT GTT GCT CTG GGC CAC AAA GG |
| N167S | CCA ACA CTA CCA GCT ACA GCG AGA TG | CAT CTC CGC TGT AGC TGG TAG TGT TGG |
| A188G | GGA TAC AAC GCT GGA GGC CAA TAT G | CAT ATT GGC CTC CAG CGT TGT ATC C |

Briefly, DNA that encodes *T. reesei* EG III was amplified from a cDNA clone (Ward, et al., *Proc. of the Tricel Symposium on "Trichoderma reesei cellulases and other hydrolases."* Espoo, Finland 1993 Ed. Suominen, P. and Reinikanen, T. Foundation for Biotechnical and Industrial Research. 8, pp153–158; and U.S. Pat. No. 5,475,101) using PCR primers that introduced a Bgl II restriction endonuclease site at the 5' end of the egl3 gene (immediately upstream of the first ATG codon) and an Xba I site at the 3' end (immediately downstream of the "stop" codon). The amplified fragment was then digested with Bgl II and Xba I, and ligated into pUC19 digested with Bgl II and Xba I.

Variants were made in this plasmid using the QuikChange™ mutagenesis methods (Strategene). The variant genes were then subcloned into the Aspergillus expression vector pPGPT-pyrG (Berka and Barnett, Biotech.Adv. 7:127 (1989)). Vectors carrying the variant genes were then transformed into A.niger var. awamori and the resultant strains grown in shake-flask cultures (WO 98/31821).

EG II variants were then purified from cell-free supernatants of these cultures by column chromatography. Briefly, approximately 1 mL of Pharmacia Butyl Sepharose (Fast Flow) resin per 10 mg of EGIII was loaded into a disposable drip column with 0.5 M. ammonium sulfate. The column was then equilibrated with 0.05 M Bis Tris Propane and 0.05 M ammonium acetate at pH 8.

The EGIII-like cellulase containing supernatants were treated overnight with 0.18 mg/mL of endoglucanase H at 37° C. Ammonium sulfate was added to the treated supernatants to a final concentration of approximately 0.5 M. After centrifugation, the supernatant was loaded onto the column. The column was then washed with 3 volumes equilibration buffer and then eluted with 2×1 volumes of 0.05 M Bis Tris Propane and 0.05 M ammonium acetate, pH 8. Each volume of flow through was collected as a separate fraction with the EGIII-like cellulase appearing in the second fraction.

Equilibrium CD experiments were performed on an Aviv 62DS or 62ADS spectrophotometer, equipped with a 5 position thermoelectric cell holder supplied by Aviv. Buffer conditions were 50 mM bis-tris propane and 50 mM ammonium acetate adjusted to pH 8.0 with acetic acid. The final protein concentration for each experiment was in the range of 5–30 mM. Data was collected in a 0.1 cm path length cell.

Spectra were collected from 265—210 nm. Thermal denaturations were performed at 217 nm from 30 to 90° C. with data collected every two degrees. The equilibration time at each temperature was 0.1 minutes and data was collected for 4 seconds per sample.

The remainder of the pH 8.0 sample was divided into 5×400 μL aliquots. Two samples were adjusted to pH 5 and 7 with acetic acid and two others were adjusted to pH 9 and 10 with sodium hydroxide. Thermal denaturations of all five samples were performed simultaneously as described above. The melting points were determined according to the methods of Luo, et al., *Biochemistry* 34:10669 and Gloss, et al., *Biochemistry* 36:5612.

TABLE 3

Thermal stability of EGIII variants

| Amino acid substitutions | Δ $T_m$ | Tm (° C.) | Fit error |
|---|---|---|---|
| *T. reesei* EGIII | 0.00 | 54.43 | 0.20 |
| W7Y | −1.03 | 53.40 | 0.24 |
| T11S/T16I | 1.07 | 55.50 | 0.13 |
| A35S | −4.03 | 50.40 | 0.14 |
| S39N | 0.47 | 54.90 | 0.17 |
| G41A | 2.47 | 56.90 | 0.11 |
| S63V | −0.83 | 53.60 | 0.11 |
| A66N | 0.07 | 54.50 | 0.10 |
| S77G | 0.07 | 54.50 | 0.09 |
| N91D | 0.47 | 54.90 | 0.17 |
| S143T | 0.47 | 54.90 | 0.12 |
| T163S | 0.27 | 54.70 | 0.07 |
| N167S | 0.17 | 54.60 | 0.10 |
| A188G | 0.47 | 54.90 | 0.17 |

As can be seen from Table 3, most of the substitutions increased the melting point over that of wild type EGIII.

Example 4

Specific Activity of Variant EGIII Cellulases

To assay for specific activity, a NPC hydrolysis assay was used. In a microtiter plate, 100 μl 50 mM sodium acetate, pH 5.5 and 20 μl 25 mg/mL o-NPC (o-Nitrophenyl o-D-Cellobioside (Sigma N 4764)) in assay buffer was added. The plate was incubated for 10 minutes at 40° C.

Once equilibrated, 10 μL EGIII-like cellulase was added and the plate incubated at 40° C. for another 10 minutes. To quench the hydrolysis and stop the reaction, 70 1L of 0.2 M glycine, pH 10.0 was added. The plate was then read in a microtiter plate reader at 410 nm. As a guide, 10 μL of a 0.1 mg/ml solution of *T. reesei* EGIII provided an OD of around 0.3.

The concentration of EGIII-like cellulase was determined by absorbance at 280 nm where the extinction coefficient was 78711 $M^{-1}$ $cm^{-1}$ or 3.352 $g/L^{-1}$ experimentally determined by the method of Edelhoch as described in Pace, et al., *Pro. Sci.* 4:2411 (1995).

TABLE 4

Specific Activity of Variant EGIII Cellulases

| Variant | Specific Activity (relative to WT EGIII) |
|---|---|
| WT EGIII | 1.00 |
| W7Y | 1.09 |
| T11S/T16I | 1.02 |
| A35S | 0.79 |
| S39N | 0.82 |
| G41A | 0.90 |
| S63V | 0.68 |
| A66N | 1.00 |
| S77G | 1.02 |
| N91D | 0.89 |
| S143T | 0.89 |
| T163S | 0.99 |
| N167S | 0.94 |
| A188G | 0.86 |

Surprisingly, the substitutions had little or no affect on the specific activity of the variants compared to wild type EGIII.

We claim:

1. A variant EGIII cellulase comprising a substitution at a residue which is sensitive to surfactant and/or temperature stress, wherein said variant EGIII cellulase is derived from *T. reesei* EGIII cellulase.

2. The cellulase of claim 1, wherein said variant comprises a substitution or deletion at a position corresponding to one or more of residues W7, T11, T16, A35, S39, G41, S63, A66, S77, N91, S143, T163, N167 and/or, A188 in EGIII.

3. The cellulase of claim 1, wherein said variant comprises a substitution at a position corresponding to one or more of residues W7Y, T11S, T161, A35S, S39N, G41A, S63V, A66N, S77G, N91D, S143T, T163S, N167S and/or, A188G in EGIII.

4. A DNA encoding the cellulase according to claim 1.

5. A vector comprising the DNA of claim 4.

6. A host cell transformed with the vector of claim 5.

7. A method of producing a variant EGIII cellulase having improved stability and/or performance comprising the steps of:
   (a) culturing the host cell according to claim 6 in a suitable culture medium under suitable conditions to produce cellulase and;
   (b) obtaining said produced cellulase.

8. A detergent composition comprising a surfactant and a cellulase, wherein said cellulase comprises a variant EGIII cellulase comprising a substitution at residue sensitive to surfactant and/or temperature.

9. The detergent of claim 8, wherein said variant EGIII cellulase comprises a substitution or deletion at a position corresponding to one or more of residues W7, T11, T16, A35, S39, G41, S63, A66, S77, N91, S143, T163, and/or, A188 in EGIII.

10. The detergent of claim 9, wherein said variant EGIII cellulase comprises a substitution at a position corresponding to one or more of residues W7Y, T11S, T161, A35S, S39N, G41A, S63V, A66N, S77G, N91D, S143T, T163S, N167S and/or, A188G in EGIII.

11. The detergent according to claim 10, wherein said detergent is a laundry detergent.

12. The detergent according to claim 10, wherein said detergent is a dish detergent.

* * * * *

SEQUENCE LISTING

<160> NUMBER OF SEQ ID NOS: 4

<210> SEQ ID NO 1
<211> LENGTH: 232
<212> TYPE: PRT
<213> ORGANISM: T. reesei

<400> SEQUENCE: 1

Met Lys Phe Leu Gln Val Leu Pro Ala Leu I le Pro Ala Ala Leu Ala
 1               5                   10                  15

```
Gln Thr Ser Cys Asp Gln Trp Ala Thr Phe Thr Gly Asn Gly Tyr Thr
             20                  25                  30
Val Ser Asn Asn Leu Trp Gly Ala Ser Ala Gly Ser Gly Phe Gly Cys
         35                  40                  45
Val Thr Ala Val Ser Leu Ser Gly Gly Ala His Ala Asp Trp Gln Trp
 50                  55                  60
Ser Gly Gly Gln Asn Asn Val Lys Ser Tyr Gln Asn Ser Gln Ile Ala
 65                  70                  75                  80
Ile Pro Gln Lys Arg Thr Val Asn Ser Ile Ser Ser Met Pro Thr Thr
                 85                  90                  95
Ala Ser Trp Ser Tyr Ser Gly Ser Asn Ile Arg Ala Asn Val Ala Tyr
            100                 105                 110
Asp Leu Phe Thr Ala Ala Asn Pro Asn His Val Thr Tyr Ser Gly Asp
        115                 120                 125
Tyr Glu Leu Met Ile Trp Leu Gly Lys Tyr Gly Asp Ile Gly Pro Ile
    130                 135                 140
Gly Ser Ser Gln Gly Thr Val Asn Val Gly Gly Gln Ser Trp Thr Leu
145                 150                 155                 160
Tyr Tyr Gly Tyr Asn Gly Ala Met Gln Val Tyr Ser Phe Val Ala Gln
                165                 170                 175
Thr Asn Thr Thr Asn Tyr Ser Gly Asp Val Lys Asn Phe Phe Asn Tyr
            180                 185                 190
Leu Arg Asp Asn Lys Gly Tyr Asn Ala Ala Gly Gln Tyr Val Leu Ser
        195                 200                 205
Tyr Gln Phe Gly Thr Glu Pro Phe Thr Gly Ser Gly Thr Leu Asn Val
    210                 215                 220
Ala Ser Trp Thr Ala Ser Ile Asn
225                 230

<210> SEQ ID NO 2
<211> LENGTH: 702
<212> TYPE: DNA
<213> ORGANISM: T. longibrachiatum

<400> SEQUENCE: 2
atgaagttcc ttcaagtcct ccctgccctc ataccggccg ccctggccca aaccagctgt     60
gaccagtggg caaccttcac tggcaacggc tacacagtca gcaacaacct tgggggagca    120
tcagccggct ctggatttgg ctgcgtgacg gcggtatcgc tcagcggcgg ggcctcctgg    180
cacgcagact ggcagtggtc cggcggccag aacaacgtca agtcgtacca gaactctcag    240
attgccattc cccagaagag gaccgtcaac agcatcagca gcatgcccac cactgccagc    300
tggagctaca gcgggagcaa catccgcgct aatgttgcgt atgacttgtt caccgcagcc    360
aacccgaatc atgtcacgta ctcgggagac tacgaactca tgatctggct tggcaaatac    420
ggcgatattg gccgattggg tcctcacag gaacagtca acgtcggtgg ccagagctgg    480
acgtctacta ctggcacaa cggagccatg caagtctatt cctttgtggc cagaccaac    540
actaccaact acagcggaga tgtcaagaac ttcttcaatt atctccgaga caataaagga    600
tacaacgctg caggccaata tgttcttagc taccaatttg gtaccgagcc cttcacgggc    660
agtggaactc tgaacgtcgc atcctggacc gcatctatca ac                        702

<210> SEQ ID NO 3
<211> LENGTH: 234
<212> TYPE: PRT
<213> ORGANISM: T. reesei
```

-continued

<400> SEQUENCE: 3

```
Met Lys Phe Leu Gln Val Leu Pro Ala Leu Ile Pro Ala Ala Leu Ala
 1               5                  10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
 50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 4
<211> LENGTH: 234
<212> TYPE: PRT
<213> ORGANISM: H. schweinitzii

<400> SEQUENCE: 4

```
Met Lys Phe Leu Gln Val Leu Pro Ala Ile Leu Pro Ala Ala Leu Ala
 1               5                  10                  15

Gln Thr Ser Cys Asp Gln Tyr Ala Thr Phe Ser Gly Asn Gly Tyr Ile
            20                  25                  30

Val Ser Asn Asn Leu Trp Gly Ala Ser Ala Gly Ser Gly Phe Gly Cys
        35                  40                  45

Val Thr Ser Val Ser Leu Asn Gly Ala Ala Ser Trp His Ala Asp Trp
 50                  55                  60

Gln Trp Ser Gly Gly Gln Asn Asn Val Lys Ser Tyr Gln Asn Val Gln
65                  70                  75                  80

Ile Asn Ile Pro Gln Lys Arg Thr Val Asn Ser Ile Gly Ser Met Pro
                85                  90                  95

Thr Thr Ala Ser Trp Ser Tyr Ser Gly Ser Asp Ile Arg Ala Asn Val
            100                 105                 110

Ala Tyr Asp Leu Phe Thr Ala Ala Asn Pro Asn His Val Thr Tyr Ser
        115                 120                 125
```

```
Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Thr Trp
145                 150                 155                 160

Thr Leu Tyr Tyr Gly Tyr Asn Gly Ala Met Gln Val Tyr Ser Phe Val
                165                 170                 175

Ala Gln Ser Asn Thr Thr Ser Tyr Ser Gly Asp Val Lys Asn Phe Phe
            180                 185                 190

Asn Tyr Leu Arg Asp Asn Lys Gly Tyr Asn Ala Gly Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```